US00PP31622P2

(12) United States Plant Patent
Albani

(10) Patent No.: US PP31,622 P2
(45) Date of Patent: Mar. 31, 2020

(54) POINSETTIA PLANT NAMED 'REALSPLEN'

(50) Latin Name: *Euphorbia pulcherrima*
Varietal Denomination: Realsplen

(71) Applicant: Albani Vincenzo e Ruggieri Italina S.S.A., Rome (IT)

(72) Inventor: Miriana Albani, Rome (IT)

(73) Assignee: ALBANI VINCENZO E RUGGIERI ITALINA S.S.A., Rome (IT)

( * ) Notice: Subject to any disclaimer, the term of this patent is extended or adjusted under 35 U.S.C. 154(b) by 0 days.

(21) Appl. No.: 16/501,350

(22) Filed: Mar. 28, 2019

(51) Int. Cl.
*A01H 5/02* (2018.01)
*A01H 6/38* (2018.01)

(52) U.S. Cl.
USPC ..... Plt./307

(58) Field of Classification Search
USPC ..... Plt./302, 303, 307
See application file for complete search history.

*Primary Examiner* — Susan McCormick Ewoldt
(74) *Attorney, Agent, or Firm* — Barbara Campbell; James M. Weatherly; Cochran Freund & Young LLC

(57) ABSTRACT

A new *Poinsettia* plant particularly distinguished by having medium red bracts and good keeping quality is disclosed.

1 Drawing Sheet

Genus and species: *Euphorbia pulcherrima.*
Variety denomination: 'Realsplen'.

BACKGROUND OF THE NEW PLANT

The present invention comprises a new and distinct variety of *Poinsettia*, botanically known as *Euphorbia pulcherrima* and hereinafter referred to by the variety name 'Realsplen'. 'Realsplen' was derived from controlled cross pollination in April 2010 in Civitavecchia, Italy, between the female *Poinsettia* variety 'EP2453' (unpatented) and the male *Poinsettia* variety 'EP8765' (unpatented).

In December 2012, a single plant having red bracts was selected in Civitavecchia, Italy. In June 2016, 'Realsplen' was first asexually propagated by vegetative apical cuttings in Stuttgart, Germany. 'Realsplen' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Medium sized red bracts; and
2. Good keeping quality.

DESCRIPTION OF THE PHOTOGRAPH

This new *Poinsettia* plant is illustrated by the accompanying photograph which shows an overall view of the whole plant. The photograph is of a plant approximately 12 weeks old grown indoors in Stuttgart, Germany in December 2016. The colors shown are as true as can be reasonably obtained by conventional photographic procedures.

DESCRIPTION OF THE NEW VARIETY

The following detailed descriptions set forth the distinctive characteristics of 'Realsplen'. The data which define these characteristics were collected from asexual reproductions carried out in Stuttgart, Germany. Data was collected on plants aged approximately 18 weeks-old after potting and grown in a glass greenhouse in Stuttgart, Germany in November 2018. Color references are to The R.H.S. Colour Chart of The Royal Horticultural Society of London (R.H.S.), 5$^{th}$ edition (2007) unless where otherwise stated.

Classification:
- *Family.*—Euphorbiaceae.
- *Species.—Euphorbia pulcherrima.*
- *Common name.—Poinsettia.*
- *Variety.*—'Realsplen'.

Parentage:
- *Female.*—'EP2453' (unpatented).
- *Male.*—'EP8765' (unpatented).

Growth:
- *Blooming habit.*—Intermittent.
- *Flowering response time.*—Approximately 50 days.
- *Keeping quality.*—Good.

Plant description:
- *Form.*—Triangular.
- *Growth habit.*—Upright.
- *Height.*—26.0 cm to 28.0 cm.
- *Width.*—30.0 cm to 35.0 cm.
- *Average number of inflorescences per plant.*—5 to 6.

Propagation:
- *Type cuttings.*—Apical cuttings.
- *Time to produce a rooted cutting.*—4 weeks.
- *Rooting habit and root color.*—Freely branching and white.

Lateral branches:
- *Color.*—RHS 143C.
- *Length.*—Approximately 25.0 cm.
- *Internode length.*—1.2 cm to 3.0 cm.
- *Diameter.*—0.5 cm to 0.7 cm.
- *Branching habit.*—Freely branching.
- *Number of lateral branches per plant.*—5 to 6.
- *Texture.*—Smooth.
- *Strength.*—Medium.

Leaves:

*Quantity.*—5 to 7 per lateral branch.
*Arrangement.*—Alternate.
*Number of lobes on the leaf blade.*—0.
*Shape.*—Ovate.
*Apex.*—Acute.
*Base.*—Obtuse.
*Margin.*—Entire.
*Length.*—10.0 cm to 14.0 cm.
*Width.*—7.0 cm to 9.0 cm.
*Texture (both surfaces).*—Smooth.
*Vein color.*—Upper surface: Transparent. Lower surface: RHS 145C.
*Venation pattern.*—Reticulate.
*Variegation.*—Absent.
*Color.*—Mature foliage: Upper surface: RHS 139A. Lower surface: RHS 139D. Immature foliage: Upper surface: RHS 143B. Lower surface: RHS 144B.
*Leaf petiole.*—Length: 3.0 cm to 5.0 cm. Diameter: 0.2 cm to 0.3 cm. Color: Upper (part) surface: RHS 59A. Lower (part) surface: RHS 181A. Texture: Smooth. Strength: Medium.

Inflorescence:

*Type and habit.*—Cluster of cyathia.
*Quantity per lateral branch.*—1 compound of cyathias accompanied by bracts.
*Position relative to foliar plane.*—Above.
*Lastingness of inflorescence on the plant.*—4 weeks.
*Natural flowering season.*—Mid November.
*Diameter.*—18.0 cm to 20.0 cm.
*Height.*—Approximately 3.0 cm.
*Fragrance.*—Absent.

Bracts:

*Number of bracts per inflorescence.*—7 to 8.
*Shape.*—Ovate.
*Apex.*—Acute.
*Base.*—Obtuse.
*Margin.*—Entire.
*Size.*—Length: 8.0 cm to 10.0 cm. Width: 5.0 cm to 6.0 cm.
*Texture (both upper and lower surfaces).*—Smooth.
*Venation pattern.*—Reticulate.
*Vein color.*—Upper surface: RHS 59A. Lower surface: RHS 181B.
*Bract color.*—Upper surface: Between RHS 45B and RHS 46A. Lower surface: Between RHS 45B and RHS 46A.
*Bract petiole.*—Length: 0.5 cm to 2.0 cm. Diameter: 0.2 cm to 0.3 cm. Color: Upper (part) surface: RHS 59A. Lower (part) surface: RHS 181B. Texture: Smooth. Strength: Medium.

Cyme:

*Diameter.*—1.0 cm to 2.5 cm.
*Cyathia number.*—7 to 10 per inflorescence.
*Deformation of glands of the cyathium.*—Absent.
*Timing of opening of cyathia.*—End of November. First pollen appears in parallel to opening of the nectar cups; stigmas appear 2 weeks later.
*Cyathium.*—Shape: Ovate. Texture (inner and outer surfaces): Smooth. Diameter: 0.2 cm to 0.6 cm. Length: 0.3 cm to 0.7 cm. Color: RHS 143C.
*Peduncle.*—Color: RHS 142B. Length: 0.2 cm to 0.3 cm. Diameter: 0.1 cm. Texture: Smooth. Strength: Medium.
*Nectar cups.*—Number: 1 per cyathium. Diameter: 0.1 cm. Length: 0.3 cm to 0.4 cm. Color: Light orange (RHS 23A) in the center, changing gradually to red at the outer region. Shape: Lip-shaped. Texture (inner and outer surfaces): Smooth.

Reproductive organs:

*Stamen quantity.*—5 to 10 per cyathium.
*Stamen shape.*—Ovate.
*Filament length.*—0.2 cm.
*Filament color.*—RHS 46A.
*Pollen quantity.*—Moderate.
*Pollen color.*—RHS 12A.
*Gynoecium.*—Pistil quantity per cyathium: 1. Pistil length: 0.2 cm. Stigma form: Divided in 2 parts. Stigma color: RHS 183A. Style length: 0.2 cm. Style color: RHS 183A. Ovary length: 0.05 cm. Ovary color: RHS 143C.

Fruit and seed set: None observed.

Disease and pest resistance: No special disease or pest resistance observed.

COMPARISON WITH PARENTAL AND KNOWN VARIETY

'Realsplen' is a distinct variety of *Poinsettia*. 'Realsplen' differs from the female parental line in that the female parent has large bracts whereas 'Realsplen' has medium bracts. 'Realsplen' differs from the male parental line in that the male parent has vigorous growth whereas 'Realsplen' has medium, compact growth.

'Realsplen' is distinguished from commercial line 'Premium Red' (unpatented) in that 'Realsplen' has medium bracts, and medium sized cyathias, whereas 'Premium Red' has large bracts and large sized cyathias.

I claim:

1. A new and distinct variety of *Poinsettia* plant designated 'Realsplen' as illustrated and described herein.

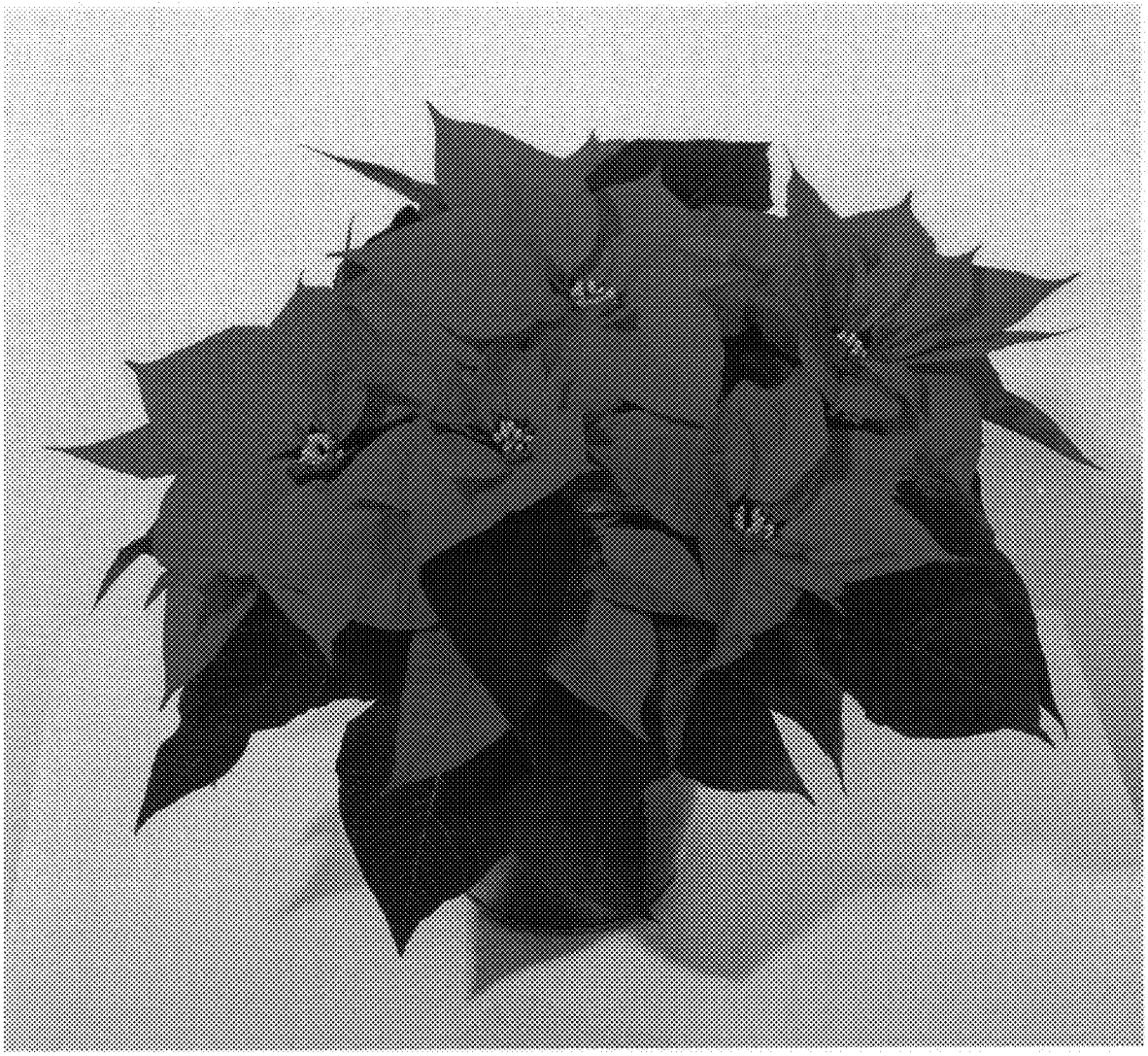

* * * * *